US008329024B2

(12) United States Patent
Henry

(10) Patent No.: US 8,329,024 B2
(45) Date of Patent: Dec. 11, 2012

(54) ELECTROCHEMICAL DEVICE AND METHOD FOR LONG-TERM MEASUREMENT OF HYPOHALITES

(75) Inventor: Kent Douglas Henry, Laramie, WY (US)

(73) Assignee: ADA Technologies, Inc., Littleton, CO (US)

( * ) Notice: Subject to any disclaimer, the term of this patent is extended or adjusted under 35 U.S.C. 154(b) by 191 days.

(21) Appl. No.: 12/831,005

(22) Filed: Jul. 6, 2010

(65) Prior Publication Data
US 2011/0000797 A1   Jan. 6, 2011

Related U.S. Application Data

(60) Provisional application No. 61/223,216, filed on Jul. 6, 2009.

(51) Int. Cl.
*G01N 27/404* (2006.01)

(52) U.S. Cl. ............ 205/778.5; 205/782; 204/402; 204/416; 204/400

(58) Field of Classification Search .......... 204/416–418, 204/400, 433, 402; 205/778.5, 779, 782, 205/789
See application file for complete search history.

(56) References Cited

U.S. PATENT DOCUMENTS

| | | | |
|---|---|---|---|
| 3,956,094 A * | 5/1976 | Capuano | 204/402 |
| 4,025,693 A | 5/1977 | Milne | |
| 4,033,830 A | 7/1977 | Fletcher, III | |
| 4,258,090 A | 3/1981 | Moraru | |
| 4,605,473 A * | 8/1986 | Dewald | 205/780 |
| 4,822,474 A | 4/1989 | Corrado | |
| 4,851,163 A | 7/1989 | Stanton et al. | |
| 5,162,077 A * | 11/1992 | Bryan et al. | 204/402 |
| 5,770,039 A * | 6/1998 | Rigney et al. | 205/789 |
| 5,791,308 A * | 8/1998 | Carter et al. | 123/145 A |
| 6,054,030 A | 4/2000 | Pierangela et al. | |
| 6,233,471 B1 * | 5/2001 | Berner et al. | 600/345 |
| 6,238,555 B1 | 5/2001 | Silveri et al. | |
| 6,270,680 B1 | 8/2001 | Silveri et al. | |

(Continued)

FOREIGN PATENT DOCUMENTS
JP   06-249832   *  9/1984

OTHER PUBLICATIONS

JPO computer-generated English language translation of the claim section and Detailed Description of Taisuke Nakano JP 06-249832 A.*

(Continued)

*Primary Examiner* — Alex Noguerola
(74) *Attorney, Agent, or Firm* — Sheridan Ross PC

(57) ABSTRACT

A method and apparatus measures the presence of total residual oxidant species in aqueous environments. More specifically, the apparatus is operable to measure hypohalites (e.g., hypochlorite and hypobromite) in water containing halide salts using electrochemistry. The apparatus can be a sensor having four electrodes—a reference electrode, a working electrode, and two auxiliary electrodes. The fourth electrode, i.e., the second auxiliary electrode, can be used to generate ionized water near and in contact with the working electrode. The ionized water can clean the working electrode to minimize effects due to scaling or biofilm formation. As such, the working electrode does not need the capability to clean itself. Thus, other elements, originally believed to be unsuitable for use in saline aqueous environments, can be used for the electrodes, for example, gold.

21 Claims, 9 Drawing Sheets

Bottom View

U.S. PATENT DOCUMENTS

| | | | |
|---|---|---|---|
| 8,150,703 B2* | 4/2012 | Cox et al. | 704/503 |
| 8,150,783 B2* | 4/2012 | Gonsalves et al. | 706/10 |
| 2008/0156658 A1 | 7/2008 | Herrington et al. | |
| 2009/0014329 A1 | 1/2009 | Silveri | |

OTHER PUBLICATIONS

"Researchers achieve breakthrough in development of ultraviolet light-emitting diodes: New Sandia UV LEDs emit short-wavelength, high-power output," Sandia National Laboratories New Release, Nov. 18, 2003, http://www.sandia.gov/news-center/news-releases/2003/elect-semi-sensors/uvleds.html.

"Ultraviolet Dechlorination Technology," Water Quality Products, Jul. 2002, vol. 7, No. 7, excerpted at http://www.wwdmag.com/Ultraviolet-Dechlorination-Technology-article3172.

"Wastewater Technology Fact Sheet: Dechlorination," EPA 832-F-00-022, Sep. 2000.

"Wastewater Technology Fact Sheet: Ultraviolet Disinfection," EPA 832-F-99-064, Sep. 1999, http://www.epa.gov/owmitnet/mtb/uv.pdf.

Bakker et al., "A Generalized Mechanism for Bacterial Adhesion to Surfaces: A Myth?" Chapter 7 of Dissertation, Applied and Environmental Microbiology, pp. 127-132, http://dissertations.ub.rug.nl/FILES/faculties/medicine/2004/d.p.bakker/c7.pdf.

Bott, A.W,, "Practical Problems in Voltammetry 3: Reference Electrodes for Voltammetry," Current Separations, 1995, vol. 14(2), pp. 64-68.

NAVSEA News Wire, "Chlorination System reduces Bio-Fouling of Sub Equipment in Littoral Water," Naval Sea Systems Command Public Affairs Office, Washington DC, Apr. 16, 2004, available at http://www.globalsecurity.org/military/library/news/2004/04/mil-040416-navsea02.htm.

Štulík et al., "Microelectrodes. Definitions, Characterization, and Applications," International Union of Pure and Applied Chemistry, Pure Appl. Chem., 2000, vol. 72(8), pp. 1483-1492.

Willemsen, P.R, "Biofouling in European Aquaculture: Is There an Easy Solution?" TNO Science and Industry, Corrosion and Fouling Prevention, for the Collective Research on Aquaculture Biofouling (CRAB), 2005, retrieved at http://www.crabproject.com/client/files/Paper_Willemsen.pdf.

Zhao, Q. et al., "Development and Evaluation of Ni—Cu—P—PTFE Composite Coatings to Minimize Microbial Adhesion," ECI Symposium Series, vol. RP2: Proceedings of 6th International Conference on Heat Exchanger Fouling and Cleaning—Challenges and Opportunities (Hans Müller-Steinhagen et al., eds.), Engineering Conferences International, Kloster Irsee, Germany, Jun. 5-10, 2005.

International Search Report for International (PCT) Patent Application No. PCT/US10/41071, mailed Oct. 26, 2010.

Written Opinion for International (PCT) Patent Application No. PCT/US10/41071, mailed Oct. 26, 2010.

ADA Technologies, Inc., Invention Disclosure Form, Jun. 24, 2008, revised Jul. 2, 2009, 14 pages.

Author Unknown, "Commands for Pronghorn SDB01," Feb. 26, 2010, 4 pages.

Author Unknown, "Electrochemical Cells that TRO electronics can operate" illustration, Dec. 9, 2009, 1 page.

Author Unknown, "Electronics Circuit involved with the sensor connection" illustration, Jan. 26, 2010, 6 pages.

Author Unknown, "Microprocessor Command Sequence for long-term sensor operation," Pronghorn Technologies, LLC, May 6, 2010, 2 pages.

Del Campo et al., "Improved free chlorine amperometric sensor chip for drinking water applications," Analytica Chimica Acta, 2005, vol. 554, pp. 98-104.

Henry, "Fabrication of a Sprial Gold Working Electrode," Pronghorn Technologies, Jan. 2010, 7 pages.

Henry, "Gold TRO Sensor Measurement Interval versus Flow Results," Pronghorn Technologies, LLC, May 21, 2010, 20 pages.

Henry, "SBIR Phase I Progress Report, CLIN 0001 AC," Pronghorn Technologies, LLC, Apr. 29, 2010, 65 pages.

Henry et al., "SBIR Contract Overview/Sensor for Continuous Detection and Reporting of Total Residual Oxidant," Pronghorn Technologies, LLC, Apr. 4, 2010, 55 pages.

Henry, "Sensor Analog Board (SAB) FW TestSequence for Development Summary," Pronghorn Technologies, LLC, Mar. 12, 2010, 3 pages.

Iketake et al., "Fabrication of a residual chlorine sensor using a gold electrode," Bunseki Kagaku, 2000, vol. 49(12), Abstract, 1 page.

International Preliminary Report on Patentability for International (PCT) Patent Application No. PCT/US2010/041071, mailed Jan. 19, 2012 6 pages.

* cited by examiner

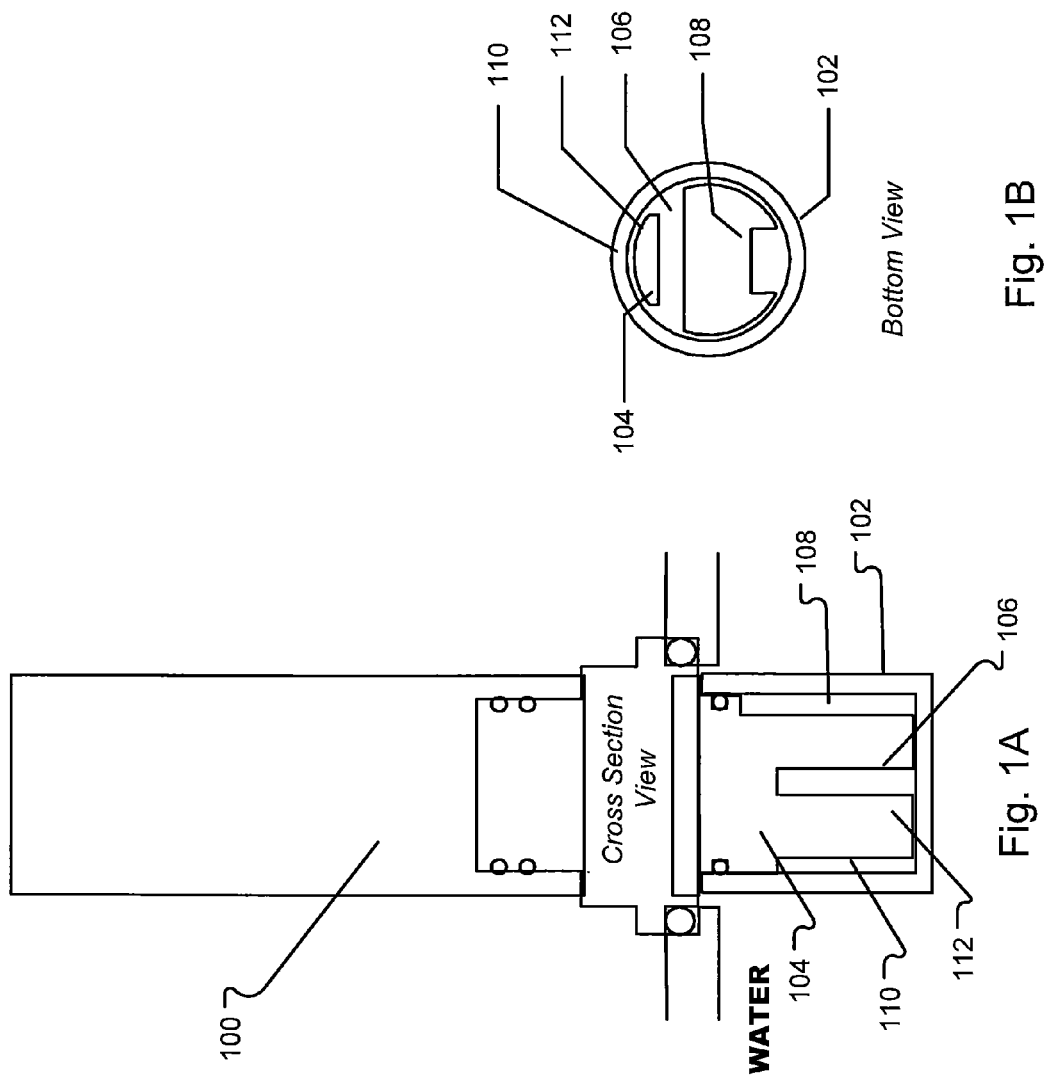

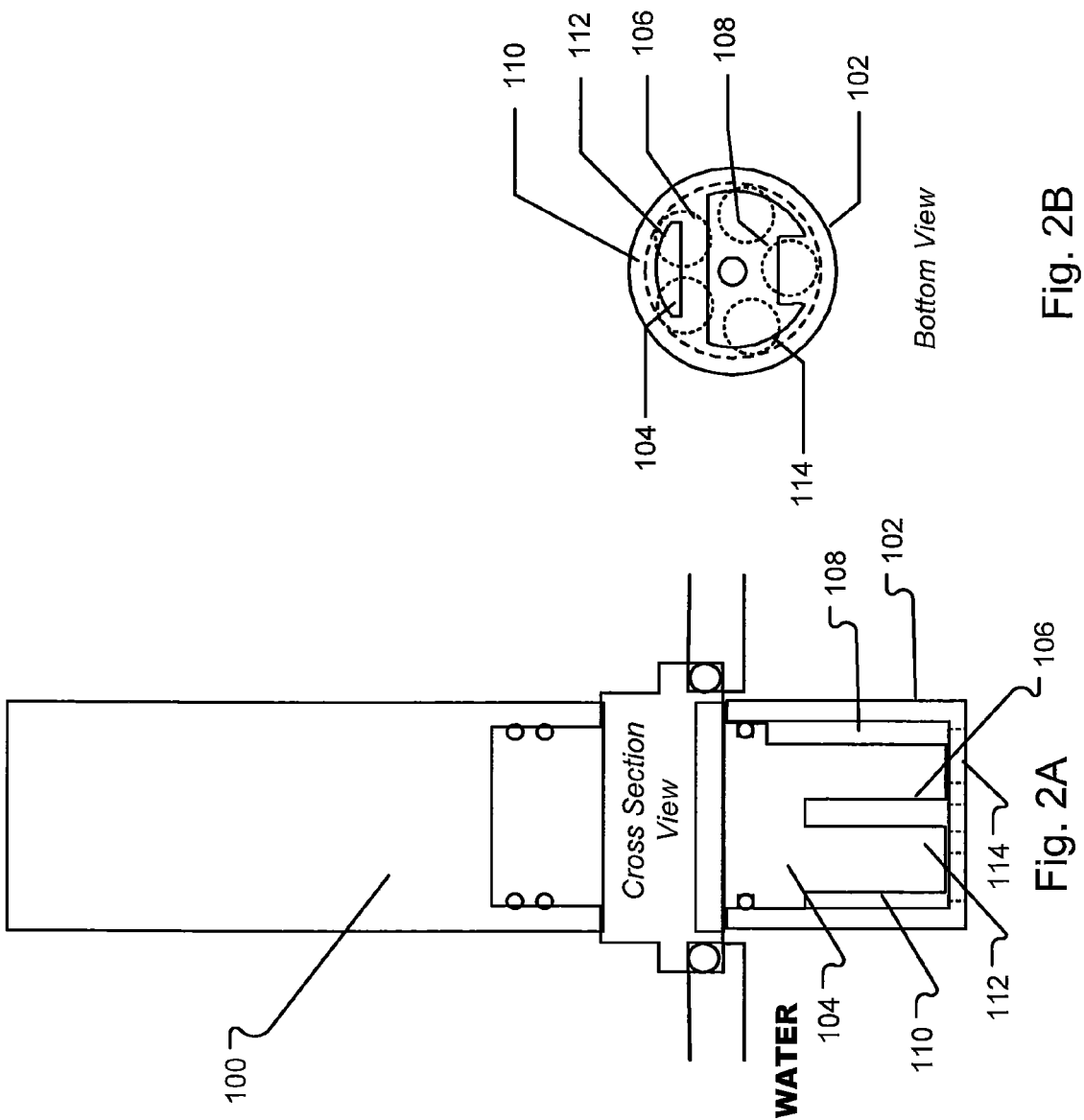

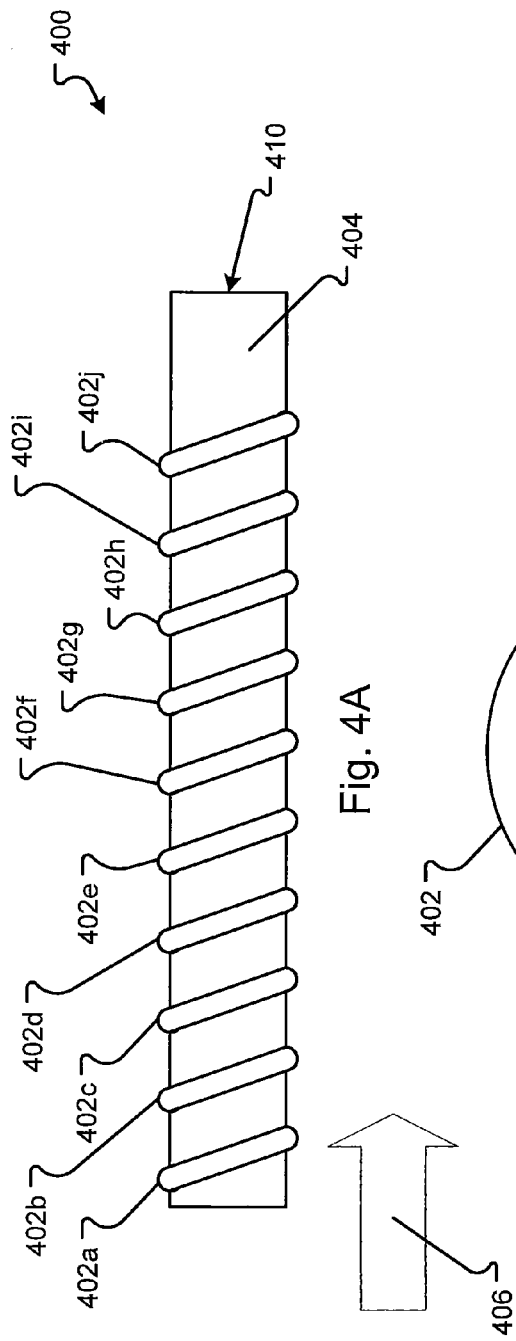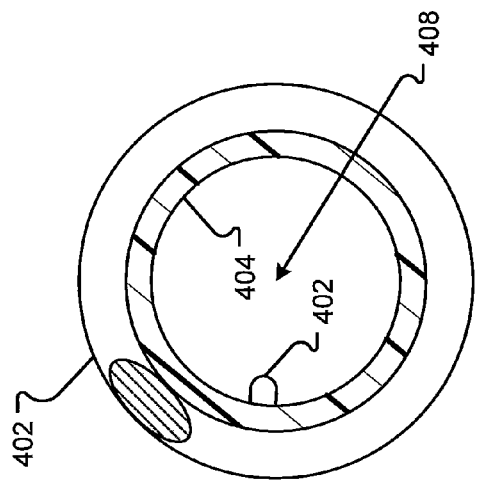
Fig. 4A
Fig. 4B

ELECTROCHEMICAL DEVICE AND METHOD FOR LONG-TERM MEASUREMENT OF HYPOHALITES

CROSS REFERENCE TO OTHER APPLICATIONS

This application claims priority to provisional patent application 61/223,216, filed Jul. 6, 2009, which is incorporated herein by reference in its entirety for all that it teaches.

BACKGROUND

The practice of eliminating unhealthy/biofouling microorganisms in water dates back to ancient civilizations. There are several methods to disinfect water, including brackish water, waste water and cooling water. Electrochemical methods can produce disinfection agents. Disinfection is not sterilization. Disinfection refers to the deactivation of "pathogen" (disease causing) microorganisms, whereas sterilization refers to the deactivation of all microorganisms present. Mechanisms for microorganism deactivation include the modification of, or attack on: the cell wall (e.g., rupture, property modification, etc.); the cell internal components (e.g., protoplasm or nucleic acid modification, alteration of protein synthesis, fatal induction of abnormal redox processes, etc.); and the enzymatic activity.

The most common disinfecting agents have properties as oxidants. This makes the disinfectants useful for the deactivation of most microorganisms, but also brings about undesirable effects, such as the discoloration of dyes, the corrosion of some metals, and the attack on some organic substances. These spurious properties of oxidants in some applications create an extra "load" thereby requiring the production of extra amounts of the disinfecting agent, increasing the corresponding costs, or requiring care to maintain the disinfecting agent concentration below levels that can cause damage, increasing collateral costs associated with treatment. Furthermore, some disinfecting agents produce "disinfection by-products" (DBP) upon their addition or reaction with organic substrates. Such DBP's are frequently toxic, as is the case with most chlorinated hydrocarbons. The main disinfectant agents produced via electrochemistry can be classified according to the oxidizing element: chlorine-based (e.g., chlorine gas, hypochlorite, hypochlorous acid, and chlorine dioxide); oxygen-based (e.g., ozone, hydrogen peroxide, and hydroxyl radicals); and others (e.g., permanganate, ferrate, ions of other transition metal ions (for example, copper and silver), percarbonate, persulfate, other halogens (for example, hypobromite, hypobromous acid) and derivatives (for example, mixed chlorine and bromine oxides), and the electrochemical manipulation of pH (i.e., the production of high levels of acidity or basicity)).

Reliable measurement of disinfection agents, especially chlorine-based or bromine-based hypohalites, has proven difficult in some circumstances. Automated water sampling systems can grab water samples for manual titration. However, this process is time consuming, does not produce near real-time measurements, and may not be performed in inaccessible systems. In some situations, sensors, based on amperometry, can be used. Amperometry is a generic term for a measurement that consumes the analyte and produces a measurable current that can be correlated to an amount of hypohalite or total residual oxidant in the solution. Total residual oxidant (TRO) measurement is often referred to as the measurement of an oxidant species or, more specifically, the measurement of chlorine using an electrochemical sensor or a titration-based approved standard method. Laypersons refer to electrolytic halogenation as chlorine, chlorination, or electrolytic chlorine generation (ECG) without particular attention to actual speciation.

However, finding the proper sensor to use for long-term measurement of TRO, especially in saline aqueous environments, has been difficult. Current chlorine amperometry sensors are not able to make functional long-term measurements without frequent and costly maintenance and calibration. In electrochemistry two or more electrodes may make a sensor that provides a measurement. The TRO sensor is a minimum three-electrode sensor that is also an amperometric sensor. Current amperometric sensors have many drawbacks.

SUMMARY

Embodiments presented herein are generally directed to a method and apparatus to measure the presence of total residual oxidant species in saline aqueous environments. More specifically, the apparatus is operable to measure hypohalites (hypochlorite and hypobromite) in water containing halide salts using electrochemistry. The apparatus can be a sensor having four electrodes—a reference electrode, a working electrode, and two auxiliary electrodes. The fourth electrode, i.e., the second auxiliary electrode, can be operated as an alternate working electrode and used to generate ionized water near and in contact with the working electrode. The ionized water can clean the working electrode to minimize effects due to scaling or biofilm formation. As such, the working electrode does not need the capability to clean itself. Thus, other elements, originally believed to be unsuitable for use in saline aqueous environments, can be used for the working electrode, for example, gold.

The embodiments provide four electrodes, i.e., one working electrode, two auxiliary electrodes, and one reference electrode, that are operated and positioned in a fashion to maximize the surface stability and sensitivity of the working electrode to hypohalites (total residual oxidant). In embodiments, the working electrode is not an active participant in the cleaning steps but is cleaned by being electrically isolated from the electrochemical circuitry and being in intimate proximity to the fourth electrode.

The use of alternating electrodes allows the working electrode to be isolated from the circuit and, when positioned in substantial proximity to the auxiliary electrode and operated against electrode four to create changes in the water, clean the working electrode without degrading the working electrode. The electrical conditions required to clean the working electrode cannot be achieved by the working electrode directly because the metallic surface will dissolve into the saline water when operated at the potentials necessary to affect the water ionization for cleaning. However, by placing the working electrode in substantial proximity to the auxiliary electrode and then operating the auxiliary electrode in conjunction with electrode four, with the working electrode electrically isolated, varying pH can be achieved to maintain the surface of the working electrode. Thus, the working electrode can be made from sensitive metals.

This cleaning of the working electrode maintains the metallic surface of the working electrode in a fairly constant surface condition that provides for long-term measurement stability as a result of stable surface conditions. Typical metallic working electrodes suffer changes in the electrode condition such as surface oxidation, roughening or fouling that cause the measurement calibration to drift over time requiring the sensor to be either routinely cleaned, recalibrated, or both. In other embodiments, amperometric sensors use semi-permeable membranes to isolate the metallic electrodes from the saline water resulting in the need to further maintain the fragile, semi-permeable membrane.

The apparatus and method provide several advantages:
1) The ability to measure chlorine and bromine hypohalites (aqueous HOX and OX—, where X=Cl or Br), which hereafter may be referred to as total residual oxidant species;
2) Improved stability and operational life of the precious metal working electrode while either simultaneously or sequentially using the same electrode configuration to assess salinity (a value that is important to electrolytic generator efficiency, generation output, and maintaining sensor stability);
3) The ability to directly and accurately measure total residual oxidant with negligible sensitivity to water flow and thereby eliminate the need for the sensor to be installed in a controlled flow sampling loop;
4) New sensor operational algorithms that compensate the total residual oxidant sensor response based on simple and robust complimentary readings such as salinity and temperature;
5) A sensor package design that allows for electrode substitution at manufacturing to take advantage of both state-of-the-art electrode arrays and low-cost, conventional macro electrodes for the working and auxiliary electrodes;
6) A sensor package that provides for flow insensitive measurement without need for a mechanical means to invoke a controlled flow;
7) Sensor communication to an external device to create a stop flow, or controlled reduced flow, condition that allows for a consistent measurement;
8) A sensor package that provides for a mechanical means to invoke flow, or sample non-flowing water, for a fast response in non-flowing environments;
9) Electrode switching to facilitate cleaning and maintenance of the critical working electrode for stable long-term operation with minimal loss of the electrode surface;
10) Very low pulse measurement of the working electrode to minimize and eliminate measurement sensitivity to varying water flow conditions; and
11) Employment of a micro-scale wire to create a microelectrode at considerably lower cost and complexity to conventional microelectrode arrays (additionally, this novel microelectrode may be placed within the tubular cavity with an auxiliary electrode or a fourth electrode for purposes as previously described).

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "in communication with" as used herein refers to any coupling, connection, or interaction using electrical signals to exchange information or data, using any system, hardware, software, protocol, or format.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term hypohalite can mean any salt of a hypohalous acid, having a general formula M(OX)n.

The term analyte can mean any substance undergoing analysis.

A sensor can mean any arrangement of two or more electrode operable to analyze an analyte.

An electrode can mean a collector or emitter of electric charge in a sensor.

BRIEF DESCRIPTION OF THE DRAWINGS

The present disclosure is described in conjunction with the appended figures:

FIGS. 1A and 1B are diagrams of an embodiment of a sensor;

FIG. 2A through 2B are diagrams of another embodiment of a sensor;

FIGS. 4A and 4B are diagrams of an embodiment of microwire electrode;

Figures 3A, 3B:
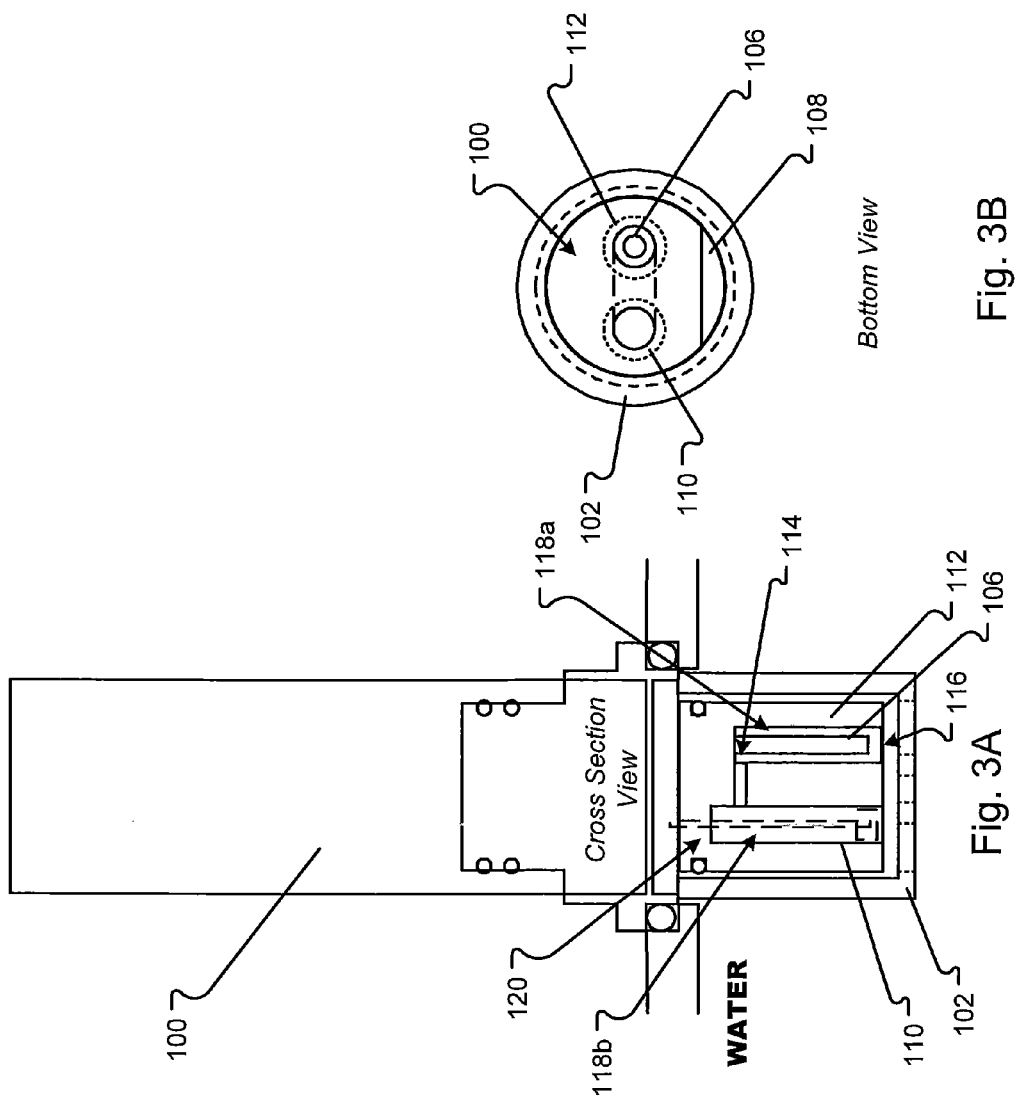
FIGS. 3A and 3B are diagrams of still another embodiment of a sensor.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION

The ensuing description provides embodiments only, and is not intended to limit the scope, applicability, or configuration of the claims. Rather, the ensuing description will provide those skilled in the art with an enabling description for implementing the embodiments. It being understood that various changes may be made in the function and arrangement of elements without departing from the spirit and scope of the appended claims.

An embodiment of a sensor 100, for measuring TRO, is shown in FIGS. 1A and 1B. The sensor is composed of four electrodes 106, 108, 110, and 112. The four electrodes can be contained within an enclosure 102. In embodiments, the enclosure 102 is a flow restriction that is substantially formed from of a nonconductive and nonreactive compound (e.g., a plastic or ceramic material). The enclosure 102 may form a barrier between the sensor and the surrounding environment. The example enclosure 102 has the following physical dimensions: external diameter of 25.40 mm (1.0"), internal diameter of 21.43 mm (27/32"), nominal wall thickness of 2 mm, internal height of 18 mm, total cup height of 32 mm, and total internal volume of 6.492 cm$^3$ (mL) These physical dimensions are exemplary as various other designs for the enclosure are possible.

The four electrodes include a working electrode 106, a reference electrode 108, a first auxiliary electrode 110 and a second auxiliary electrode 112 (also referred to as electrode four). The working electrode 106 can aid in measuring TRO in the aqueous solution. The working electrode 106 is the location at which reduction of the oxidant species takes place when the working electrode 106 is biased at an appropriate reduction potential with respect to the reference electrode 108. The working electrode 106 may be a metal, for example platinum or gold. Thus, when the working electrode 106 is biased at a value of less than +0.3 V versus a reference electrode 108, the working electrode's 106 surface will reduce hypohalites and produce a current proportional to concentration of the hypohalites and other environmental parameters, such as water flow. A gold surface on the working electrode 106 may be necessary to detect hypochlorite, whereas a graphite surface has been used to detect hypobromite. In an embodiment, the working electrode 106 is a gold microdisk array, such as the ABTECH MDEA 050 gold microdisk array sold by ABTECH Scientific, Inc. The microdisk array may have a diameter of approximately 7.5 mm and contain 5,184 discs each with a diameter of 50 μm producing a total electrochemical area of 10.17 mm$^2$.

The first auxiliary electrode 110 is often called the counter electrode. The working electrode 106 is the electrode on which the reaction of interest occurs, and through which measurements are taken. The auxiliary electrode 110 changes in polarity opposite to that of the working electrode 110, but the current and polarity of auxiliary electrode 110 are not measured. The auxiliary electrode 110 exists to ensure that current does not run through the reference electrode 108 and often has a surface area much larger than that of the working electrode 106 to ensure that the reactions occurring on the working electrode 106 are not surface area limited by the counter electrode 110. In the example shown in FIG. 1B, the auxiliary electrode 110 may be made of platinum black and be at least a 3.6 mm diameter disc having an area of 10.17 mm$^2$.

The reference electrode 108 is an electrode that has a standard, stable electrochemical potential (half-cell potential) that is used as a voltage standard against which voltages are applied to the working electrode 106. In the example in FIG. 1A and FIG. 1B, the reference electrode 108 can be a mesh of silver wire anodized with Ag/AgCl having an effective height of 10 mm and a width of 7 mm. This robust solid-state reference electrode is optimal for saline waters, such as seawater. In low to non-saline water conditions, a traditional double junction reference electrode may be used with some environmental limitations to the sensor operation with respect to shock, vibration, temperature, pressure and other parameters, known to those skilled in the art.

The second auxiliary electrode or electrode four 112 is novel. Electrode four 112, at times, acts as a supplemental auxiliary electrode that functions in parallel to the auxiliary electrode 110. (to increase the total surface area of the functional auxiliary electrode). At other times, electrode four 112 acts as a working electrode in place of the normal working electrode 106 to clean the normal working electrode 106. Here, electrode four 112 creates a higher potential, e.g., above 0.7 volts, to ionize the solution that is in contact with the working electrode 106. The ionized water has attributes of either high or low pH. Thus, the basicity or acidity of the water acts to "clean" the surface of the working electrode 106. Electrode four 112 can be made of materials suitable to function as an electrode. In embodiments, electrode four 112 is made of glassy carbon and is a disk having a diameter of 5 mm with an area of 19.6 mm$^2$.

In prior art sensor development, −0.5 V is used as the negative potential pulse and +0.7 V as the positive potential pulse on the working electrode. The −0.5 V is not sufficient to generate hydrogen, and the +0.7 V is not positive enough to generate oxygen in seawater allowing for a stable long-term cleaning action. Thus, at the prior art voltages, the working electrode would become fouled by biofilm. Further, the working electrode could not be gold if the working electrode was to clean itself, as was common in three electrode systems. The positive potential that may be applied to the working electrode is limited by the gold surface employed for increased sensitivity to chlorine. At a potential more positive than 0.7 V, gold is dissolved (oxidized) away in the presence of chloride.

To function properly, electrode four 112 is introduced in close or intimate proximity to the working electrode 106. In embodiments, electrode four 112 may be used to clean the surface of the working electrode 106. The intimate proximity of the working electrode 106 and electrode four 112 depends on the flow of the solution, the level of potential created at electrode four 112, the shape and size of the enclosure 102, etc. The embodiment shown in FIG. 1B includes a separation or barrier 104 that creates two volumes of solution within enclosure 102. The separation 104 allows electrode four 112 to change the chemistry of the solution in the first volume and the second volume but in opposite ways. If electrode four 112 creates an acidic solution in the first volume housing electrode four 112, an opposite reaction (e.g., creating a basic solution) will occur in the second volume. The separation design can also affect the functioning of electrode four 112 with respect to cleaning. The dimensions provided for the embodiment in FIGS. 1A and 1B represents one example of an operational sensor 100.

Another embodiment of the sensor 100 is shown in FIGS. 2A and 2B including the four electrodes 106, 108, 110, and 112 and the enclosure 102. Here, the enclosure 102 includes one or more openings 114 in the bottom of the enclosure 102. The solution can pass through the openings 114 in this embodiment to allow measurement of a flowing solution.

Another embodiment of the sensor 100 is shown in FIGS. 3A-3B including the four electrodes 106, 108, 110, and 112 and the enclosure 102. Here, the enclosure 102 also includes one or more openings 114 and 116 to allow the mechanically activated flow of solution across the working electrode 106. The solution can pass through the openings 114 and 116, in this embodiment, by means of a plunger 120 to allow measurement of a non-flowing, stagnant solution.

The reference electrode 108 is positioned outside of the enclosure. A unique microwire working electrode 106 is position within a first channel 118a while the auxiliary electrode 110 is position within the second channel 118b. An embodiment of the microwire electrode 106 is described in conjunction with FIGS. 4A and 4B. Electrode four is also positioned within the first channel further upstream than the working electrode 106. In this way, ionized solution can flow from electrode four 112 and to or past the working electrode 106.

An embodiment of a microwire electrode 400 is shown in FIGS. 4A and 4B. The microwire electrode 400 includes a microwire 402 formed into a helix. The microwire can be 50 μm diameter gold wire (Alpha Aesar). The helix has windings

402a through 402j. A winding can be a single revolution of the wire in the helix. There may be more or fewer windings than those shown in FIG. 4A. In one embodiment, there are 27 windings. Wrapping microwire into a helix is a much lower cost fabrication means for producing a sensitive measurement microelectrode.

Figure 8:
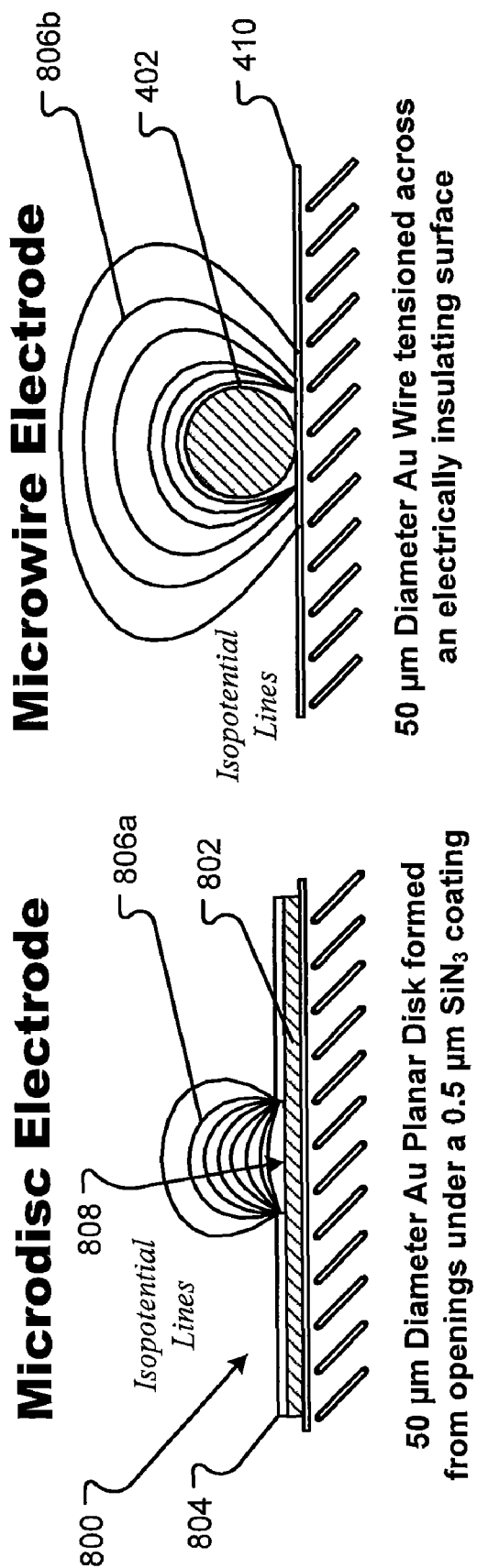
FIGS. 8A and 8B are diagrams of an embodiment of a microdisk and a microwire electrode showing isopotential lines.

Further, the microwire electrode 400 can produce greater electrical fields compared to the microdisk electrode. Referring to FIGS. 8A and 8B, a microdisk electrode 800 is shown in FIG. 8A. Here, the electrode conductor (e.g., gold electrode) 802 is covered by an insulation insulating layer 804 that has one or more holes or openings 808 formed in the insulation layer 084. When charged under a potential, the microdisk electrode 800 can create an electrical field (shown as a set of isopotential lines) 806a at each opening 808.

Figure 9:
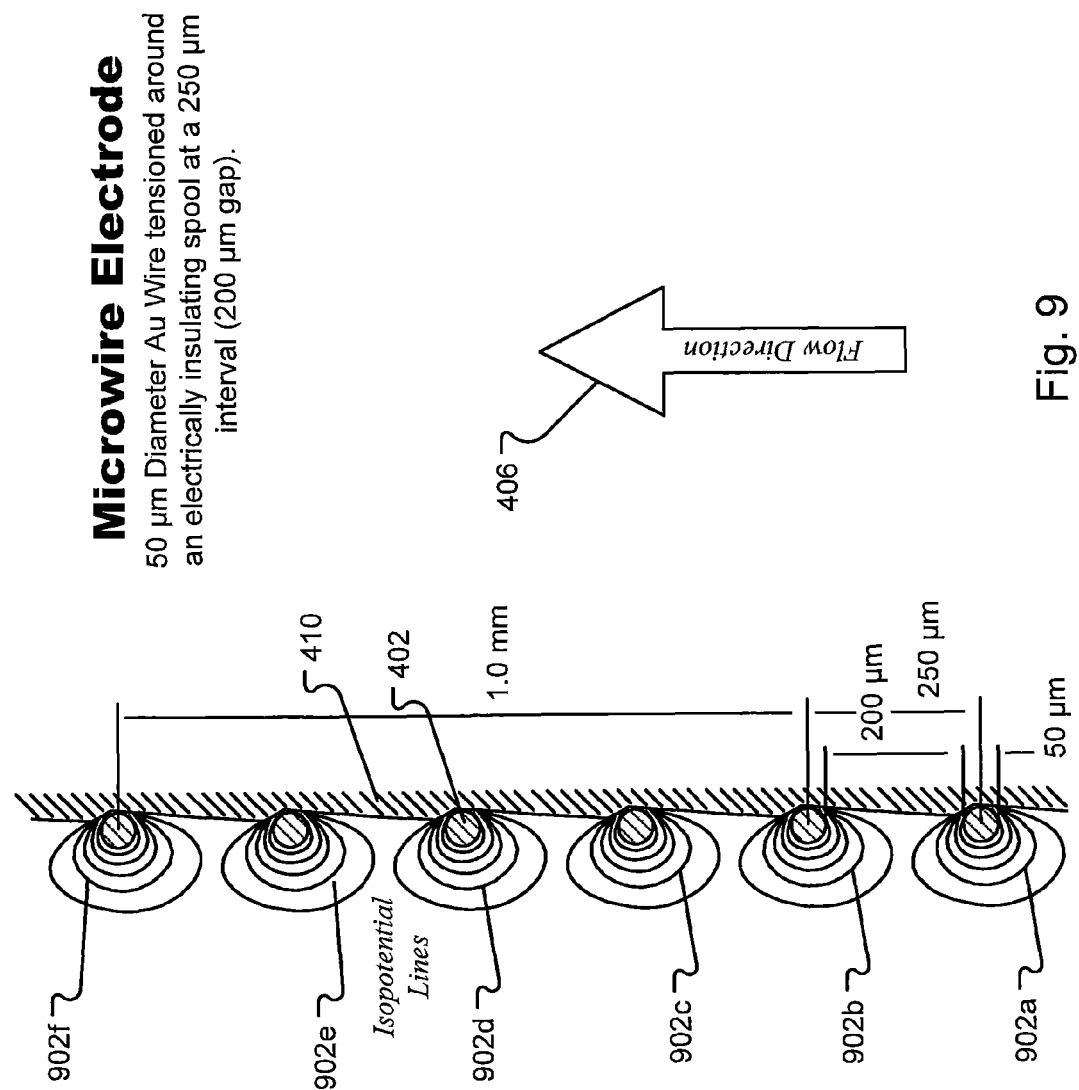
FIG. 9 is a diagram of an embodiment of a microwire electrode showing isopotential lines.

The a single winding of the microwire electrode 402 is shown in FIG. 8B. Under the same electrical charge, the microwire electrode can create a larger electrical field (shown as a set of isopotential lines) 806b than the opening of the microdisk electrode opening 808. The winding of the microwire electrode 402 exhibits a large penetration of the isopotential field lines 806b into the analyte containing solution. Thus, each winding of the microwire electrode 402 can be more sensitive than each opening 808 of the microdisk electrode 800. Another diagram of the microwire electrode 402 is shown in FIG. 9. Here, the large electrical field, represented by isopotential lines 902, is compounded or increased because of the several windings used in the microwire electrode. Other shapes are possible for the winding or shaping of the microwire. The microwire can be a conductive substance, for example, gold and platinum.

In embodiments, the helix may be supported by or affixed on a substructure 404 as shown in FIG. 4A. The substructure can be a pipe or lumen constructed of a rigid material, for example, plastic. A grove is formed into the substructure 404 in a spiral that holds the helix 402 of microwire. In this way, the microwire maintains the helical shape. A first end of the micro wire may be passed through an opening in the substructure 404, as shown in FIG. 4B, to travel through the lumen in the substructure to an electrical connection. The other end of the microwire may also make an electrical connection. As such, the microwire can form a circuit and function as an electrode 106.

The dimensions in the microwire electrode dictate how the microwire will perform. The diameter of the microwire, the spacing of the windings of the helix, and the rate of the flow 406 of the solution past the microwire sensor 400, the potential applied to the microwire, and the measurement duration are important to the function of the microwire electrode 400 based sensor. As the electrode 400 measures hypohalites, the electrical potential created on the microwire 402 can cause some of the hypohalite to be consumed. The consumption of the hypohalite can cause errant readings on windings further downstream if the solution, with the consumed hypohalite, passes the windings. If the measurement time interval (i.e., the period between successive measurements) is set at a predetermined level that is sufficiently short (which is based on flow rate, potential created at the microwire windings, the diameter of the microwire, the distance between the microwire windings, etc.), the microwire electrode 400 can result in measurement insensitivity to flow rate. Thus, the factors mentioned above must be controlled and determined to create a functioning microwire sensor. One skilled in the art will understand how the factors interact and how to change the winding distance to create a functioning sensor.

Figure 5:
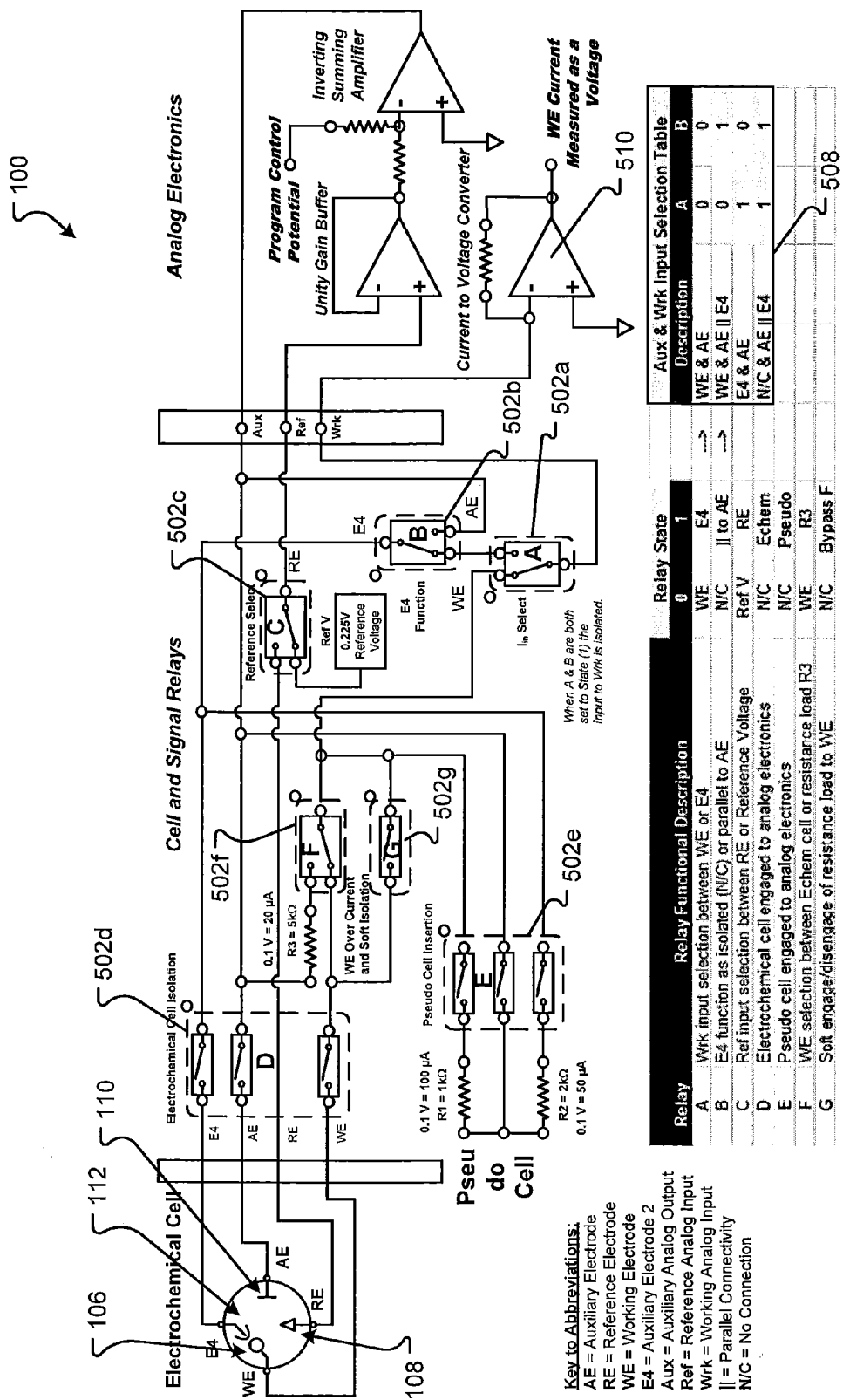
FIG. 5 is block diagram of an electric circuit of a sensor.

An electrical diagram of an embodiment of the sensor 100 is shown in FIG. 5. The sensor 100 operates similarly to existing three electrode sensors when measuring hypohalites. One exception is that electrode four 112 can be used in conjunction with the first auxiliary electrode 110 to create a single "functional" auxiliary electrode with greater surface area. However, the differences with three electrode sensors is more focused on the operation of electrode four 112.

The sensor 100 can include at least one switch 502a and 502b. Switch 502a and switch 502b can work in concert to place the sensor 100 either into a measurement configuration or a cleaning configuration. With switch A 502a in a position 0 and switch B 502b in a position 0 or 1 (table 508) the sensor 100 is in a measurement configuration and can measure a current, or a current as a potential, to determine an amount of hypohalite in the solution in which the electrodes reside. With switch A 502a in a position 0 and switch B 502b in a position 0 (table 508) the sensor cleans the working electrode 106. In this configuration, the working electrode 106 "floats," that is, the working electrode 106 is neither connected to a power source or to ground. Further, electrode four 112 is connected to a power source to create a potential at electrode four 112. The potential at electrode four 112 electrolytically creates either an acid or a base solution (depending on whether the potential is positive or negative) that cleans the working electrode 106. The acidic or basic solution may be alternated during successive or subsequent cleanings Electrochemical(ly) can mean of or relating to a chemical reaction brought about by electricity. Electrolytically means produced by or used in the process of the producing of chemical changes by passage of an electric current through an electrolyte. The configuration of the sensor 100 can be oscillated or switched back and forth between measurement and cleaning.

Figure 6:
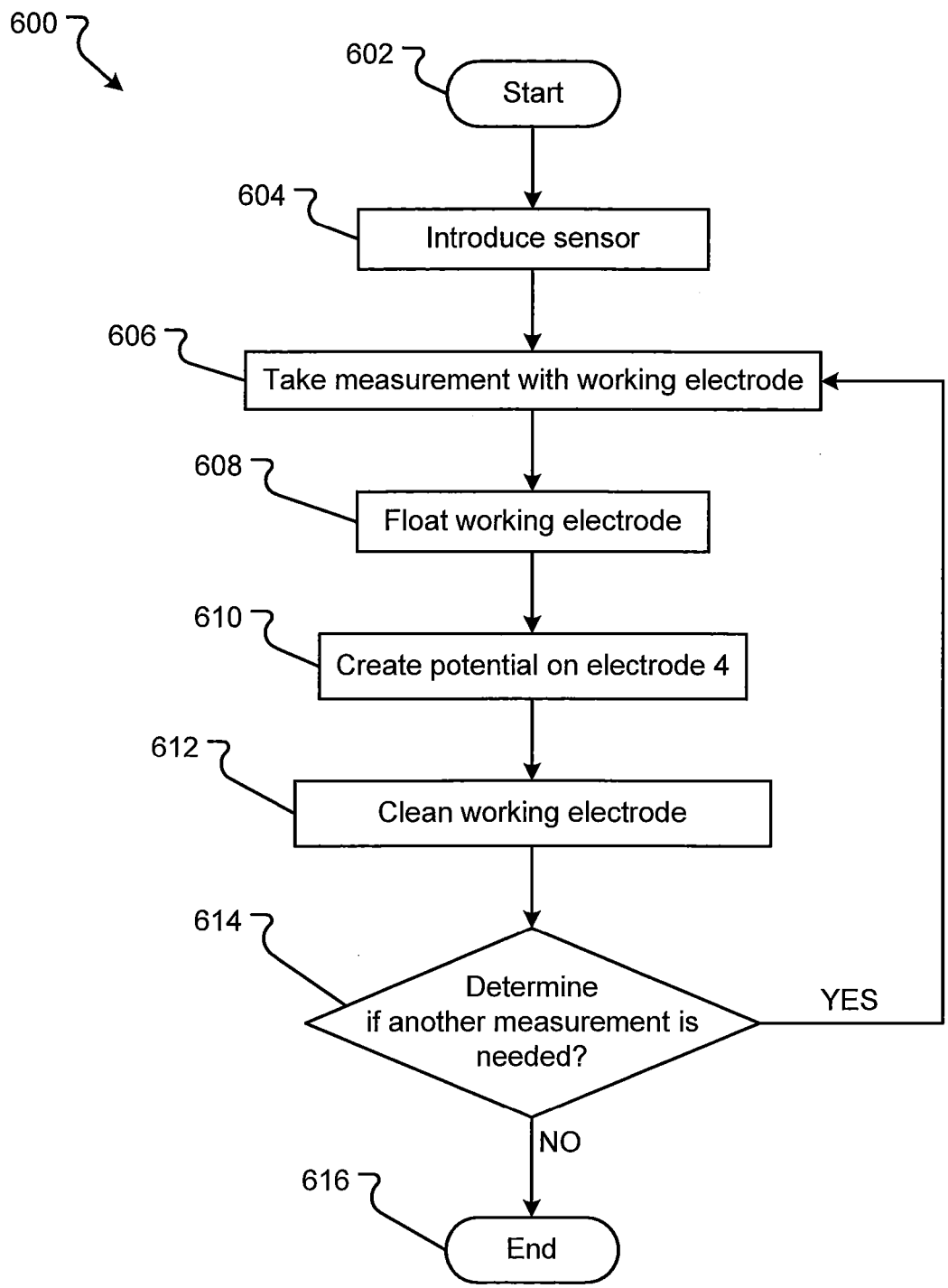
FIG. 6 is a flow diagram of an embodiment of a process for measuring total residual oxidant in an aqueous environment.

An embodiment of a method 600 for operating the four electrode sensor 100 is shown in FIG. 6. Generally, the method 600 begins with a start operation 602 and terminates with an end operation 616. While a general order for the steps of the method 600 are shown in FIG. 6, the method 600 can include more or fewer steps or arrange the order of the steps differently than those shown in FIG. 6. Some or all the steps in method 600 can be executed as a set of computer-executable instructions executed by a computer system and encoded or stored on a computer readable medium. Hereinafter, the method 600 shall be explained with reference to the systems, components, devices, etc. described in conjunction with FIGS. 1-5.

The function of the four-electrode, amperometric sensor 100 is to alternate the sensor operation between modes of (1) oxidant measurement, (2) conductivity measurement, (3) proton generation near the working electrode 106 and (4) hydroxyl generation near the working electrode. Since the working electrode 106 cannot participate in the hydrolysis events (because gold dissolves in chloride environments when energized above +0.7 Volts), the second auxiliary electrode 112 is placed very close to the face of the working electrode 106 and the first auxiliary electrode 110 is placed further away.

The sensor 100 is introduced into the measurement environment, in step 604. The sensor 100 is a four electrode sensor 100. The working electrode 106 of the sensor 100 can be gold. The measurement environment may be a test environment or an actual field environment where the sensor 100 is being used. In embodiments, the environment is a saline aqueous solution that may contain hypohalites, which may be chlorine or bromine based. The saline aqueous solution may be seawater.

The sensor 100 can take a measurement using the working electrode 106, in step 606. In the measurement of total residual oxidant the ideal electrode material for the working electrode 106 is gold. However, gold has an upper bound on the applied potential, if this potential is exceeded, the gold is electrochemically dissolved into the solution as noted above. In the measurement mode, switches 502 are set to the position where the two auxiliary electrodes 110 and 112 are connected in parallel and act as a single larger area auxiliary electrode. In some embodiments, only one of the auxiliary electrodes 110 or 112 is connected. A measurement of total residual oxidant, with a reduction of the analyte at the working electrode 106, results in a current passing through the working electrode 106 that is proportional to the analyte concentration. This current is converted to a potential, by a current to voltage converter 510, and subjected to conversion to a digital value for processing by a microprocessor as is understood by those skilled in the art.

The sensor 100 can transition to a cleaning mode. In the cleaning mode, the analog switches 502 are set to the position where the working electrode 106 is electrically isolated from the circuit. In other words, the sensor 100 configuration floats the working electrode 106, in step 608. Further, in the configuration, electrode four 112 takes on the function of the working electrode.

An electrical potential is then created on electrode 4 112, in step 610. Cleaning of the working electrode 106 (where the halogen reduction occurs) can be performed electrochemically through the application of alternating negative and positive potentials to electrode 4 112. Calcium and magnesium can solidify onto electrode surfaces but the mechanism for elemental precipitation, as hydroxides, on any surfaces may also apply for the electrodes. The cycling of alkaline and acidic conditions at the electrode surface have been previously shown to prevent hydroxides from precipitating and thus can keep the electrode clean. Hydrogen evolution occurs at a negative potential and oxygen evolution occurs at a positive potential. The change in pH can clean the contaminants precipitated from water onto the working electrode 106, in step 612. Thus, the intimate proximity of the working electrode 106 and electrode 4 112 is important to allow the generated hydroxyls and protons to flow over and clean the gold surface of the working electrode 106. Further, the potential applied to electrode 4 112 may need to be greater than +1.0 V to generate sufficient protons and less than −1.0V to generate sufficient hydroxyls to effect the surface cleaning.

The system in communication with the sensor 100 may then determine if another measurement is needed, in step 614. In embodiments, the system takes periodic measurements with the sensor 100. In this situation, the system determines if the period of time between measurements has elapsed and starts the process of measurement again. In other embodiments, the system is directed by input from a human tester. A human tester may direct a measurement. If a directive is received, the system starts the process of measurement again. If a new measurement is needed, the process 600 flows "YES" back to step 606. If a new measurement is not needed, the process 600 flows "NO" to end operation 616.

Using this process repeatedly, the sensor 100 can reach equilibrium and provide quick and effective measurement of TRO in saline aqueous solutions. The concentration of hypohalites may then be adjusted (by adding chemicals, through electrochemical means, etc.) according to the measurements. The adjustments may then be verified through method 600. In this way, disinfection, and possibly sterilization, of the aqueous solution can occur.

Figure 7:
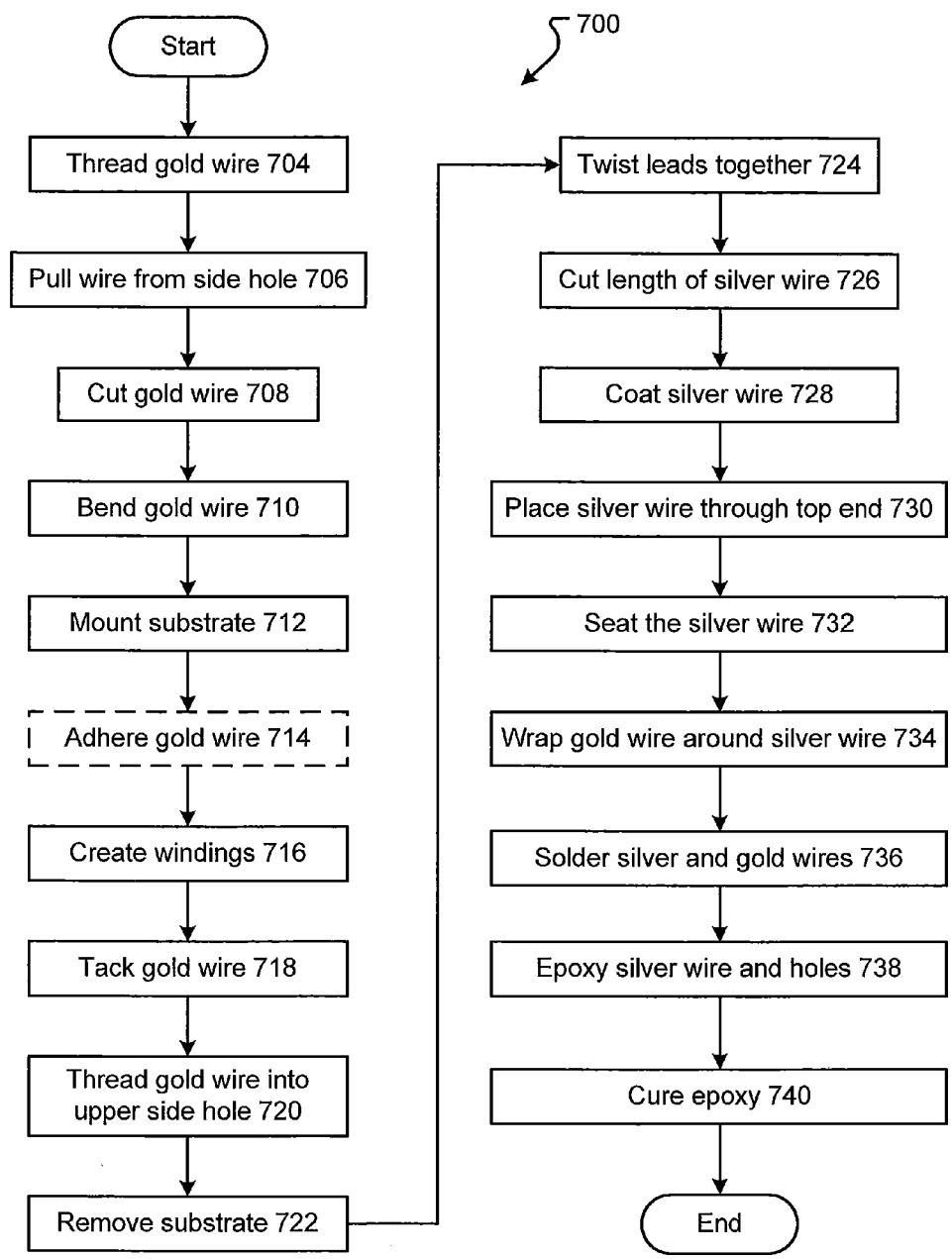
FIG. 7 is a flow diagram of an embodiment of a process for manufacturing a microwire electrode.

An embodiment for manufacturing a microwire electrode 400 is shown in FIG. 7. Thread a length of gold wire 402 (e.g., 50 μm diameter gold wire (Alpha Aesar)) through the lumen 408 of the substructure 404 from the top opening 410 through and out a hole formed in the side of the substructure, in step 704. A stereo microscope is useful. A bent piece of 30 gauge solid wire may be employed to help "fish" the gold wire 402 out of the side hole. Pliers or tweezers should not be used to handle the gold wire 402. If platinum wire is being used, it may be inserted from the bottom hole instead of the top hole based on the operator preference. Pull a length (e.g., 300 mm) of gold wire 402 out from the bottom side hole, in step 706. Cut the gold wire 402 leaving about a length (e.g., 30 mm) of gold wire 402 protruding from the top hole 410, in step 708. Bend the gold wire 402 protruding from the top hole 410 around substrate 404 so that the gold wire 402 follows the exterior of the substrate 404 and passes the gold wire 402 exiting the bottom side hole, in step 710. Tools should not be used for this operation; only use clean fingers that have been washed with non-residual soap and water.

Place the top 410 of the substrate 404 into a rotary tool that is mounted in a fixed position, in step 712. Optionally, adhere the gold wire 402 by placing a small amount of JB Weld Kwik over the gold wire 402 where the gold wire 402 exits the bottom side hole to hold the gold wire 402 in place, in step 714. Wind the substrate 404 to create the helical windings of the gold wire 402 in step 716. In embodiments, step 716 creates 27 turns of gold wire 402 on the substrate 404. Tack the gold wire 402 into place using JB Weld Kwik, in step 718. Feed the remaining gold wire 402 through an upper side hole, in step 718. It may be prudent to apply one turn after the tack location to prevent kinking the gold wire 402 during the termination steps.

Thread the remaining gold wire 402 into the upper side hole, in step 720. Thread only the amount necessary for the tip of the gold wire 402 to exit the top hole. Remove the substrate 404 from the rotary tool and pull the slack out of the gold wire 402 to make sure that the gold wire 402 is still properly seated into the upper side hole, in step 722. Twist the lead gold wires 402 together by rotating the ends of the gold wire 402, in step 724.

Cut a length of wire (e.g., 70 mm piece of 1 mm diameter silver wire), in step 726. Coat a portion of the cut wire (e.g., 20 mm of the silver wire) with epoxy, e.g., (a thin layer of Ellsworth epoxy), in step 728. Place the epoxy coated end of the silver wire into the top end 410 of the substrate 404, in step 730. Seat the silver wire into the bottom of the substrate 404, in step 732. Wrap the protruding gold wire 402 loosely around the silver wire, in step 734. Solder (e.g., using 0.15" diameter 63/37 solder) the silver wire to the gold wire 402, in step 736. Epoxy, (e.g., using Ellsworth epoxy) the silver wire and open side holes, in step 738. Cure the epoxy, in step 740.

Specific details were given in the description to provide a thorough understanding of the embodiments. However, it will be understood by one of ordinary skill in the art that the embodiments may be practiced without these specific details. For example, elements of the embodiments may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

This application contains an appendix with further materials describing the sensor 100, the microwire electrode 400, and the operation and methods described herein. The appendix is hereby incorporated as part of the application for all that it teaches.

While illustrative embodiments of the invention have been described in detail herein, it is to be understood that the inventive concepts may be otherwise variously embodied and employed, and that the appended claims are intended to be construed to include such variations, except as limited by the prior art.

What is claimed is:

1. A sensor operable to measure total residual oxidant (TRO) in an aqueous environment, comprising:
   a working electrode operable to measure TRO;
   a reference electrode;
   a first auxiliary electrode; and
   a second auxiliary electrode;
   wherein the second auxiliary electrode is configured to operate as at least one of: i) an alternate working electrode operable to clean the working electrode, ii) an auxiliary electrode electrically parallel to the first auxiliary electrode, and iii) in a single common enclosure with the working electrode, the reference electrode, and the first auxiliary electrode.

2. The sensor as defined in claim 1, wherein the working electrode and the second auxiliary electrode are in intimate proximity.

3. The sensor as defined in claim 2, wherein the working electrode is gold.

4. The sensor as defined in claim 3, wherein the working electrode is operable to be placed in electric isolation and wherein, when the working electrode is in electrical isolation, the second auxiliary electrode functions as a working electrode.

5. The sensor as defined in claim 1, wherein the reference electrode is operable to provide a reference potential in the aqueous environment, wherein the first auxiliary electrode is operable to provide a second potential in the aqueous environment, and wherein the second auxiliary electrode is operable to produce electrolytically at least one of an acid or a base to clean substantially the working electrode.

6. The sensor as defined in claim 5, wherein the working electrode is one of a microdisk or a microwire electrode.

7. The sensor as defined in claim 6, wherein the microwire electrode is a helix of gold wire.

8. The sensor as defined in claim 1, wherein the sensor comprises a potentiostat, the potentiostat in communication with the working electrode, the reference electrode, the first auxiliary electrode, and the second auxiliary electrode.

9. A microwire electrode assembly comprising:
   a helix of gold microwire, the helix comprising:
   a first end, the first end electrically connected to a sensor circuit;
   at least one winding; and
   an auxiliary electrode configured to operate as an alternate working electrode operable to clean the helix;
   wherein the helix is operable to measure total residual oxidant (TRO) in an aqueous environment and is positioned in proximity to the auxiliary electrode.

10. The microwire electrode as defined in claim 9, further comprising a substrate, wherein the helix is wound around an exterior surface of the substrate, and wherein the at least one winding comprises a first winding and a second winding.

11. The microwire electrode as defined in claim 10, wherein the substrate is a plastic tube.

12. The microwire electrode as defined in claim 9, wherein the substrate includes a spiral channel formed in the exterior surface of the plastic tube to accept the helix of gold microwire.

13. The microwire electrode as defined in claim 12, wherein the microwire electrode is in intimate proximity to a second electrode, wherein the second electrode is operable to create an ionized solution to clean the surface of the microwire electrode.

14. The microwire electrode as defined in claim 13, further comprising:
   a reference electrode; and
   an auxiliary electrode, wherein, with the microwire electrode, measures TRO.

15. The microwire electrode as defined in claim 14, wherein measurement of TRO is flow insensitive when a measurement time is set to a predetermined level.

16. A method for measuring TRO in an aqueous environment, the method comprising:
   introducing a sensor into the aqueous environment, the sensor comprising a gold working electrode, a reference electrode, a first auxiliary electrode, and a second auxiliary electrode configured to operate as a working electrode;
   measuring an amount of hypohalite in the aqueous environment; and
   cleaning the surface of the gold working electrode with one of an acid or a base produced by at least one of the first auxiliary electrode and the second auxiliary electrode.

17. The method as defined in claim 16, wherein the cleaning step comprises alternating between cleaning with the acid and cleaning with the base.

18. The method as defined in claim 17, wherein the acid and base are created through hydrolysis.

19. The method as defined in claim 18, wherein the sensor comprises:
   the gold working electrode operable to measure TRO;
   a reference electrode;
   the first auxiliary electrode; and
   a second auxiliary electrode.

20. The method as defined in claim 19, wherein the gold working electrode is a gold microwire electrode.

21. The method as defined in claim 20, wherein an aqueous environment having a flowing solution and where the gold microwire electrode measures the hypohalite without sensitivity to the flow.

* * * * *